US006653065B2

(12) United States Patent
Ganser

(10) Patent No.: US 6,653,065 B2
(45) Date of Patent: *Nov. 25, 2003

(54) METHOD AND APPARATUS FOR LASER MICRODISSECTION

(75) Inventor: Michael Ganser, Giessen (DE)

(73) Assignee: Leica Microsystems Wetzlar GmbH, Wetzlar (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/944,917

(22) Filed: Aug. 31, 2001

(65) Prior Publication Data

US 2002/0048747 A1 Apr. 25, 2002

(30) Foreign Application Priority Data

Sep. 1, 2000 (DE) .......................... 100 43 504

(51) Int. Cl.$^7$ .............................. C12Q 1/00; C12M 1/00
(52) U.S. Cl. .......................................... 435/4; 435/283.1
(58) Field of Search .................................. 435/4, 283.1

(56) References Cited

U.S. PATENT DOCUMENTS

| 5,859,699 A | * | 1/1999 | Baer et al. ................... 356/246 |
| 5,998,129 A | | 12/1999 | Schütze et al. ................. 435/4 |
| 6,100,051 A | * | 8/2000 | Goldstein et al. .......... 435/40.5 |

\* cited by examiner

Primary Examiner—Louise N. Leary
(74) Attorney, Agent, or Firm—Davidson, Davidson & Kappel, LLC

(57) ABSTRACT

A method and an apparatus for laser microdissection of specimen regions (23) of interest of a specimen (4) are described. In a first step, a perforation with webs (26, 27, 28) is generated by means of a focused laser beam (7) along a cut line (25) enclosing the specimen region (23) of interest. The perforation has at least two webs (26, 27, 28) which interrupt the cut line (25) and join the specimen region (23) of interest to the surrounding specimen (4). In a second step, the webs (26, 27, 28) are broken with a single laser pulse of the defocused laser beam (7) directed onto the specimen region (23) of interest, thereby detaching the specimen region (23) of interest from the specimen (4).

16 Claims, 3 Drawing Sheets

METHOD AND APPARATUS FOR LASER MICRODISSECTION

CROSS REFERENCE TO RELATED APPLICATIONS

This invention claims priority of the German patent application 100 43 504.1, filed Sep. 1, 2000, which is incorporated by reference herein.

FIELD OF THE INVENTION

The invention concerns a method and an apparatus for laser microdissection of specimen regions of interest of a specimen that is mounted on a specimen holder.

BACKGROUND OF THE INVENTION

"Laser microdissection" refers, in the field of biology and medicine, to a method with which a small piece is cut out from a generally flat specimen (for example cells or a tissue section) with a fine, focused laser beam. The cut-out piece is thus available for further biological or medical (e.g. histological) examinations.

U.S. Pat. No. 5,998,129 describes a method of this kind and an apparatus for laser microdissection. The specimen is arranged on a solid, planar support, for example a polymer support film, that is stretched over a glass specimen slide commonly used in laboratories. The method described operates in two steps. In a first step, a specimen region of interest—on which, for example, a selected cell grouping or a histological section is located—is cut out with a laser beam. For that purpose, the cut line of the laser beam describes a complete curve around the specimen region of interest. After cutting, the cut-out specimen region of interest is then still adhering to or resting on its substrate. In a second step, an additional laser shot is therefore directed onto the specimen region of interest, and the specimen region of interest is thereby catapulted in the direction of the laser beam into a collection vessel.

One disadvantage of the method occurs already in the first method step. Shortly before the cut line is completed, the cut-out specimen region of interest is joined to the surrounding specimen only by a narrow web. As a result of electrical charging or mechanical stress in the web, at this stage of the cut the previously cut-out specimen region of interest often swings away, i.e. out of the focal plane of the laser beam or behind the remaining support film. It is not possible to complete cutting of the swung-away specimen region of interest, since the folded-over portion of the sample region projects into the cut line and will thus be damaged upon further cutting. At the same time, transporting the cut-out specimen region away by means of a laser shot thereby becomes difficult or even impossible, since a sufficient application area for the laser shot is not present.

SUMMARY OF THE INVENTION

It is therefore the object of the invention to describe a method for laser microdissection which allows controlled detachment of a specimen region of interest from a specimen, and prevents the specimen region of interest from swinging away.

This object is achieved by a method for laser microdissection of specimen regions of interest of a specimen that is mounted on a specimen holder which according to the present invention comprises the following steps:
 a) creating a perforation with webs along a cut line enclosing the specimen region of interest by means of a focused laser beam, the perforation having at least two webs that interrupt the cut line and join the specimen region of interest to the surrounding specimen; and
 b) breaking the webs of the perforation with a single laser pulse of the defocused laser beam directed onto the specimen region of interest, thereby detaching the specimen region of interest from the specimen.

It is a further object of the invention to describe an apparatus for performing the method for laser microdissection which allows controlled detachment of a specimen region of interest from a specimen, and prevents the specimen region of interest from swinging away.

This object is achieved by an apparatus for laser cutting of microscopic specimens with a focused laser beam, which according to the present invention has the following features:
 a) a microscope having at least one objective that defines an optical axis, for viewing of a specimen having a specimen region of interest, and having a laser that generates a laser beam and at least one optical system that couples the laser beam into the objective,
 b) a cut line control unit, associated with said microscope for generating a relative movement between said laser beam focused by the objective,
 c) perforation creating means for creating a perforated cut line around said specimen region of interest, said cut line having at least two webs that join said specimen region of interest to said surrounding specimen,
 d) means for defocusing said laser beam, and
 e) web breaking means for directing a single laser pulse of said defocused laser beam onto the specimen region of interest, thereby detaching the specimen region of interest from the specimen.

For the method according to the present invention, the specimens to be examined, from which specimen regions of interest are to be cut out, are prepared on very thin plastic films. The thickness of these plastic films is on the order of between 1 and 2 $\mu$m. PET films, for example, can be used. The best cutting results have been obtained, however, with PEN films. With these it is possible to generate narrow and at the same time stable webs. It has proven particularly favorable for the method if webs having a width of approximately 1 $\mu$m are left in place. The plastic films are stretched, in known fashion, over a specimen holder. This can be, for example, a glass specimen slide commonly used in laboratories. Other specimen holders (in terms of shape and material) are, however, conceivable. The specimen holder rests on an X-Y stage which allows different specimen regions to be viewed and selected. The apparatus usually has at least one vessel in the vicinity of the specimen for collecting a cut-out specimen region of interest.

One embodiment of the apparatus according to the present invention has a stationary laser beam, and the cut line control unit comprises a displaceable X-Y stage which moves the specimen relative to the stationary laser beam during creation of a perforation. In this context, very high demands are made on the positioning accuracy of the X-Y stage in order to produce an exact cut line. The X-Y stage is preferably displaced in motorized fashion.

In another embodiment of the apparatus according to the present invention, the cut line control unit comprises a laser scanning device which moves the laser beam relative to a stationary specimen during creation of a perforation. For that purpose, the X-Y stage with the specimen holder and specimen on it is not displaced during creation of the perforation. The cut line of the perforation results exclusively from deflection of the laser beam over the specimen.

A particularly advantageous embodiment of the apparatus is one in which the means for creating a perforation comprise a laser control unit which controls the operating parameters of the laser. Those operating parameters are, for example, the laser power, the laser pulse duration, or the laser cut width. The means for creating a perforation can additionally comprise an autofocus apparatus for the laser, thereby making possible automation of the perforation operation.

In addition, the means for breaking the webs of the perforation can comprise a perforation control unit for controlling the cut line control unit and the laser control unit. It proves advantageous for this purpose if the perforation control unit additionally comprises means for defocusing the laser. A user of the apparatus for breaking the webs then no longer needs to defocus the laser manually. This defocusing constitutes an essential part of the method, since thereby the laser beam is spread out and its energy is distributed over a larger area. As a result, a cut can no longer be generated in the specimen region of interest, but the laser pulse is used to break the webs.

For laser microdissection of another specimen region of interest, focusing of the laser can then be performed very quickly and reliably by means of the autofocus apparatus. This makes possible automation of the entire method.

In other embodiments of the apparatus, means for selection of the cut line, or means for selection of the cut line and the position of the webs by a user, are provided. In addition, means can be provided for selection of the width of the webs and for selection of the position of the webs by a user. By way of this selection capability, the user can specifically select the correct specimen region of interest before creation of the perforation, and at the same time can protect important portions of the specimen from damage. For example, crack structures occur in the region of the webs between the specimen region of interest and the surrounding specimen. Because the user can, for example, place the webs on non-critical cell structures of the specimen, critical cell structures of interest within the specimen region of interest can be protected from such crack structures.

The method according to the present invention possesses the advantage of ruling out any swinging away of the specimen region of interest during cutting. Problem-free cutting of the specimen is thereby possible. In addition, reliable removal of the cut-out specimen region of interest is possible. Automation of the method and of the apparatus makes possible utilization in routine laboratory operations.

BRIEF DESCRIPTION OF THE DRAWINGS

The invention will be described in more detail below with reference to the schematic drawings, in which.

In the Figures, identical apparatus elements are labeled with the same reference numbers.

DETAILED DESCRIPTION OF THE INVENTION

Figure 1:
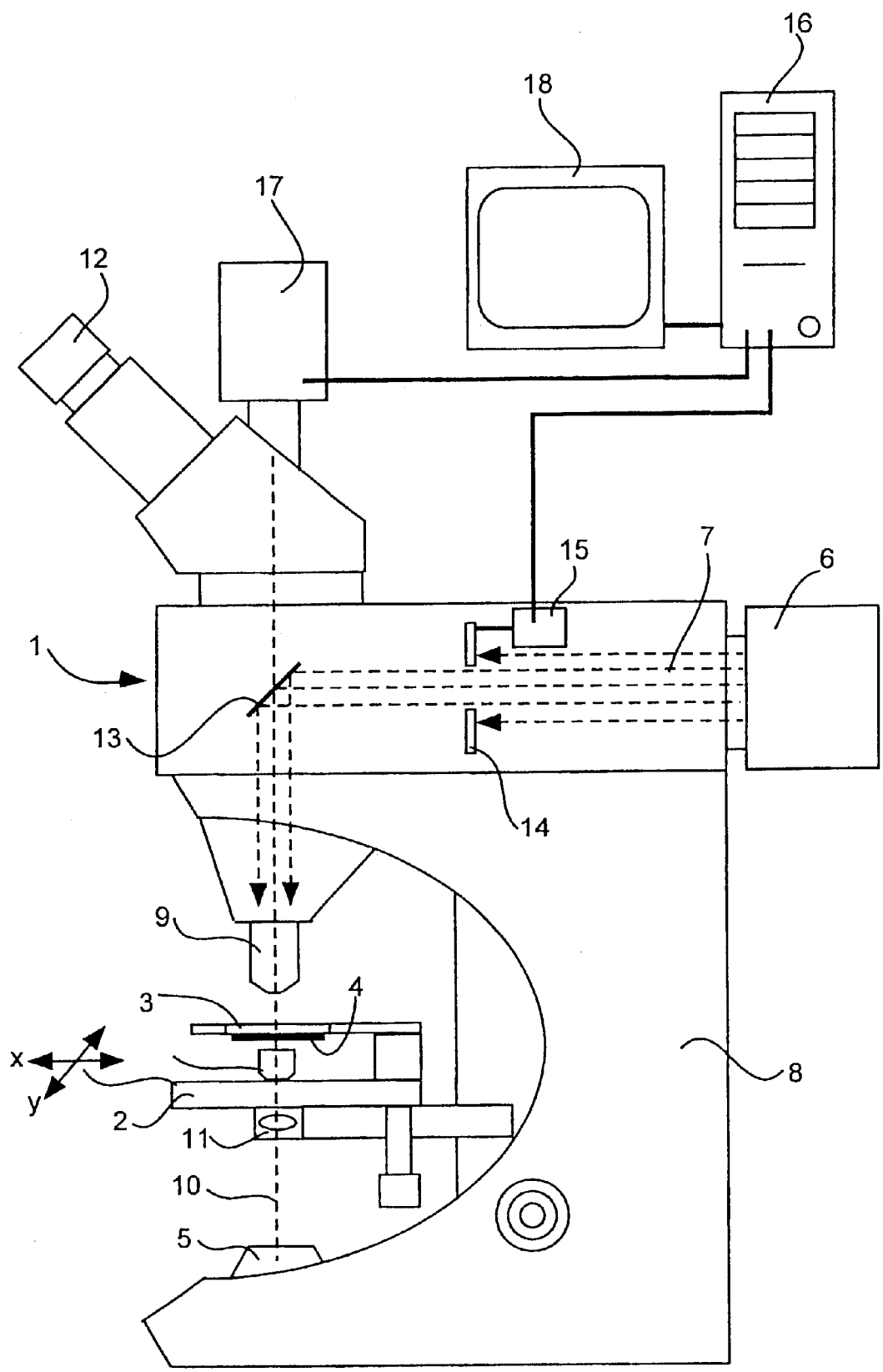
FIG. 1 shows an apparatus for laser cutting with a stationary laser beam.

FIG. 1 depicts an apparatus for laser cutting that operates with a stationary laser beam and a specimen moved relative thereto. It comprises a microscope 1 having an X-Y stage 2 displaceable in motorized fashion. X-Y stage 2 serves to receive a specimen holder 3 on which is mounted a specimen 4 to be examined or cut. Also provided is an illumination system 5, as well as a laser 6 that generates a laser beam 7 which is focused onto specimen 4 in order to cut the latter. X-Y stage 2 serves as a cut line control unit and generates, during the cutting operation, a relative movement between laser beam 7 and specimen 4.

Microscope 1 that is depicted is a transmitted-light microscope, in which illumination system 5 is arranged on a microscope stand 8 below X-Y stage 2 and specimen 4. At least one objective 9 of microscope 1 is arranged above X-Y stage 2 and specimen 4. Objective 9 defines an optical axis 10 that aligns with the optical axis of illumination system 5.

In this arrangement just described, specimen 4 is viewed with transmitted-light illumination. Laser cutting can also be performed with an inverted microscope, in which illumination system 5 is arranged above X-Y stage 2, and the at least one objective 9 is arranged below X-Y stage 2.

The light emitted from illumination system 5 is directed through a condenser 11 from below onto specimen holder 3, with specimen 4, arranged on X-Y stage 2. The light penetrating through specimen 4 arrives at objective 9 of microscope 1. Within microscope 1 the light is conveyed via lenses and mirrors (not depicted) to at least one eyepiece 12 of microscope 1, through which an operator can view specimen 4 arranged on X-Y stage 2.

In microscope stand 8 of microscope 1, an optical system 13 is provided in optical axis 10 of objective 9. Optical system 13 can be, for example, a dichroic splitter. It is furthermore conceivable for optical system 13 to comprise multiple optical components. Such is the case when laser beam 7 needs to be deflected several times. A stop 14, with which the diameter of laser beam 7 can be limited in appropriate fashion, is also provided in laser beam 7. Stop 14 can be configured, for example, as a fixed stop. In an advantageous embodiment, multiple fixed stops 14 can be arranged on a revolving disk or on a linear slider, so that one of these fixed stops can be introduced into the beam path as the particular requisite stop 14. Introduction into laser beam 7 can be performed manually by the user, or in motorized fashion.

In the embodiment depicted here, stop 14 is configured as a variable stop, for example as an iris diaphragm whose diameter is controlled via a diaphragm motor 15. Diaphragm motor 15 receives from a computer 16 the necessary control signals for setting the requisite diaphragm diameter.

Microscope 1 is furthermore equipped with a camera 17 which acquires an image of specimen 4 that is to be cut. This image can be displayed on a monitor 18 that is connected to computer 16. The system made up of computer 16, camera 17, and monitor 18 constitutes, in this embodiment, means for creating a perforation. They can be used to observe and monitor the cutting operation performed with laser 4. For example, the computer can deliver trigger signals to the laser to initiate laser pulses and to control laser power, can activate diaphragm motor 15, and can activate an autofocus device (not depicted) for laser 6.

In addition, the specimen region of interest of specimen 12 that is to be cut out can be traced around on monitor 18 using a mouse cursor. The position of the webs can be determined automatically by a software program in computer 16. It proves to be advantageous, however, if a user can also predetermine the position and width of the webs by means of a mouse click. For example, the webs can be placed in regions in which, upon subsequent breakage, cracks may occur without negatively affecting the information about the specimen region of interest. Along the cut line thereby characterized, the cutting operation by means of laser 4 is then performed and thereby the intended performation is created.

In this embodiment, a control system for automatic defocusing of laser 6, integrated into computer 16, is provided as the means for breaking the webs. In addition, the center of the specimen region of interest can be determined, from the preselected cut line, by way of a software program in computer 16. X-Y stage 2 can then be displaced in such a way that upon breakage of the webs, the stationary defocused laser beam 7 is directed onto that calculated center point.

Arranged below specimen 4 is at least one collection vessel 19 for collecting the cut-out specimen region of interest.

Figure 2:
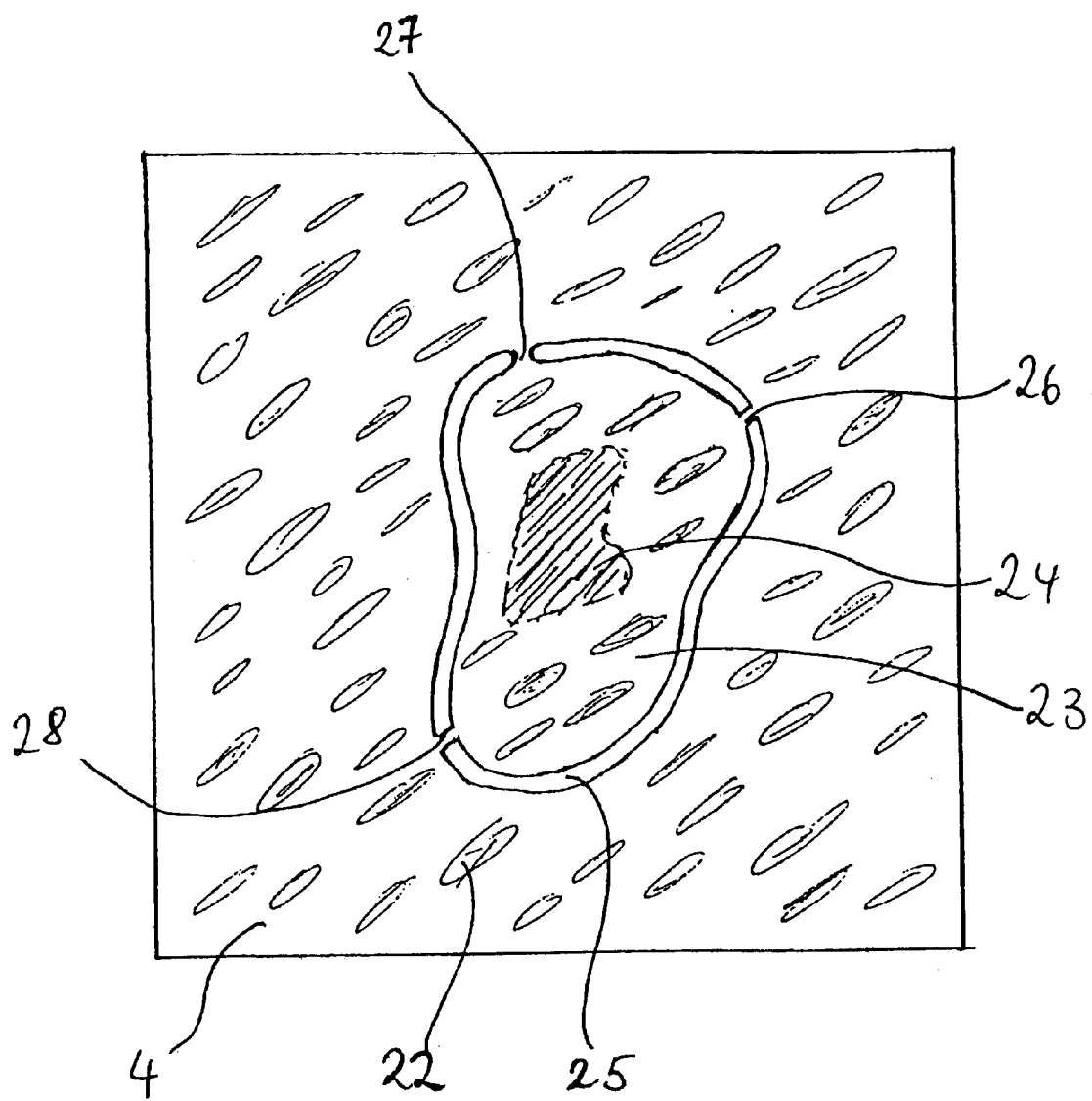
FIG. 2 shows a specimen with a perforation around a specimen region of interest.

The method according to the present invention will be described below with reference to FIG. 2.

The Figure depicts a camera image of a specimen 4 having a plurality of cells 22. Located approximately in the center of specimen 4 is a specimen region 23 of interest in which an atypical cell structure 24, e.g. a suspected cancer cell, is located. This specimen region 23 of interest is to be removed from specimen 4 for further examination.

For that purpose, a desired reference cut line for the perforation that is to be generated is marked by a user in the camera image, using a corresponding software program, by means of a computer mouse. In addition, the number and desired positions of the webs of the perforation are marked.

Corresponding to the presently set cut width of laser beam 7, a number of reference positions of laser beam 7 on specimen 4 for the defined reference cut line is calculated by computer 16, the successively arranged reference positions of laser beam 7 resulting in the desired reference cut line.

To create the perforation, the X-Y stage is then displaced in steps in such a way that laser beam 7 successively strikes the calculated reference position[s] on specimen 4. In each reference position, a respective trigger signal is generated by computer 16 and sent to laser 6, and a laser pulse is correspondingly emitted by it. In this fashion, the perforation that is depicted is generated with laser 6 around specimen region 23 of interest. The perforation comprises cut line 25 interrupted by webs 26, 27, 28. The specimen region of interest is then joined to the surrounding specimen 4 only by the three webs 26, 27, 28.

In the last method step, these webs 26, 27, 28 are broken with a laser pulse directed onto the center of specimen region 23 of interest. Specimen region 23 of interest that is dissected in this fashion drops down into a collection vessel (not depicted) arranged below it. The laser pulse for breaking webs 26, 27, 28 is preferably executed with a greatly defocused laser beam 7 in order to prevent, as much as possible, biological changes in the specimen region of interest. In particular, the spread-out laser beam rules out any perforation in the specimen region of interest.

Figure 3:
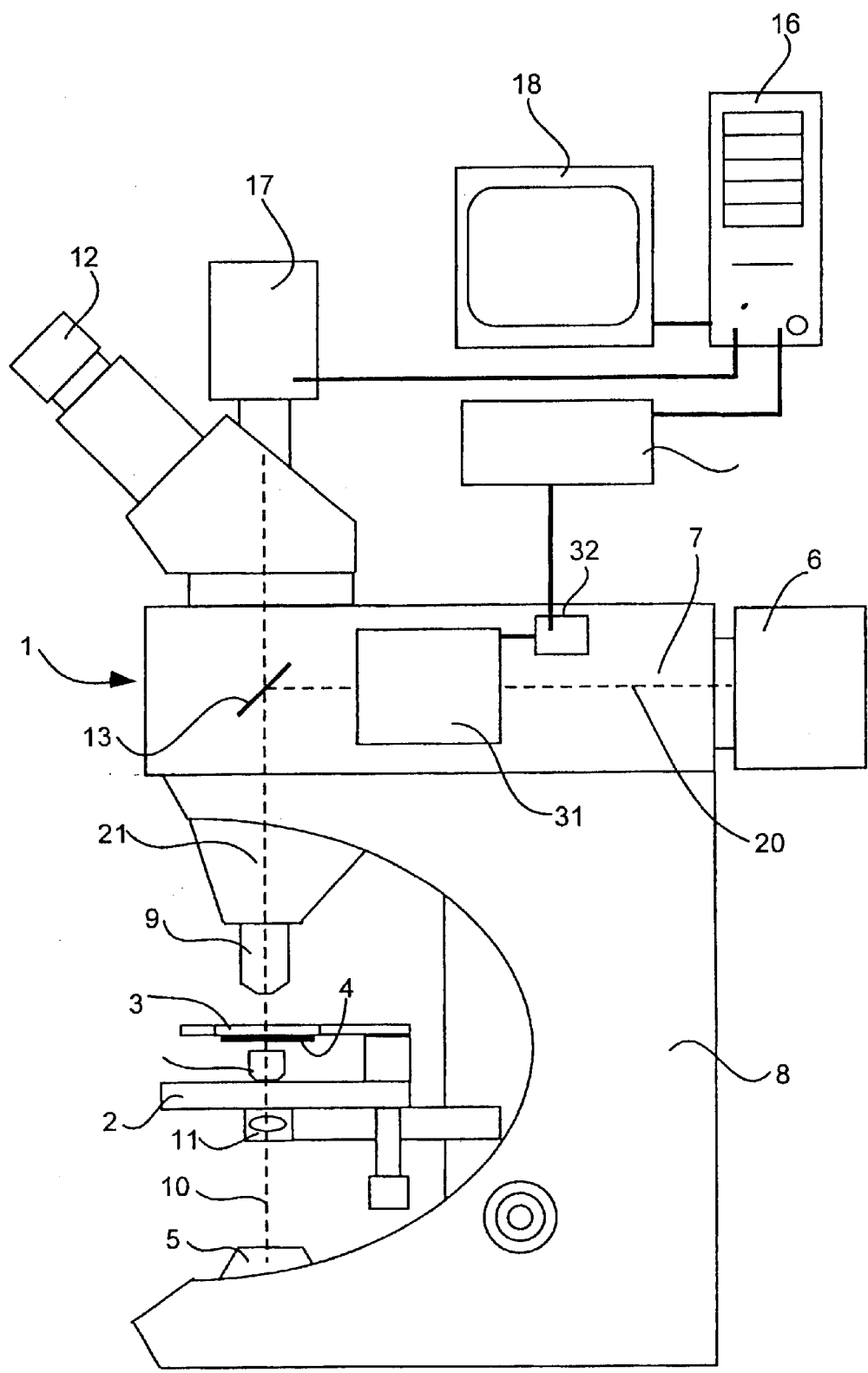
FIG. 3 shows an apparatus for laser cutting with a movable laser beam.

FIG. 3 shows a laser microdissection unit according to the present invention for carrying out the method according to the present invention, which moves a laser beam over a stationary specimen during cutting.

The laser microdissection unit comprises a microscope 1 having a displaceable X-Y stage 2 on which a specimen holder 3 is arranged. Located on the underside of specimen holder 3 is a specimen 4 to be cut. Arranged below X-Y stage 2 are an illumination system 5 and a condenser 11 which illuminates specimen 4. During the cutting operation, X-Y stage 2 is not moved horizontally, i.e. in the X and Y directions. At least one collection vessel 19, for collecting the cut-out specimen region of interest, is arranged below specimen 4.

A laser beam 7 proceeds from a laser 6 (in this example, a UV laser) and is coupled into an illuminating beam path 20. A laser scanning device 31 is arranged in illuminating beam path 20. Laser beam 7 passes through laser scanning device 31 and arrives via an optical system 13 at an objective 9 which focuses laser beam 7 on specimen 4. Optical system 13 is advantageously embodied as a dichroic splitter, through which an imaging beam path 21 proceeding from specimen 4 through objective 9 arrives at at least one eyepiece 12.

In this embodiment, the adjustment of laser scanning device 31 and therefore the displacement of laser beam 7 on specimen 4 are accomplished with means for creating a perforation which comprise a motor 32 associated with laser scanning device 31, a control unit 33, and a computer 16. Motor 32 is connected to control unit 33, which supplies the control signals for activation of motor 32. Control unit 33 is connected to computer 16, to which a monitor 18 is connected.

Laser scanning device 31 itself serves as a cut line control unit that generates, during the cutting operation, a relative movement between laser beam 7 and specimen 4. Focusing of laser beam 7 can be accomplished by a user by manually moving X-Y stage 2 vertically while simultaneously visually monitoring the camera image. An embodiment of the apparatus that comprises an autofocus apparatus (not depicted) for laser beam 7 is, however, more user-friendly.

Activation of laser scanning device 31 causes laser beam 7 to appear at the output of laser scanning device 31 at various deflection angles. By varying the deflection angle, laser beam 7 can be guided to any desired positions on specimen 4 that lie within the field of view of objective 10. By suitable activation of laser scanning device 31, a cut line is generated on specimen 4. The cut-out part of specimen 4 falls into a collection vessel 17 that is arranged below specimen 4 on X-Y stage 2.

The image of specimen 4 acquired by a camera 17 is displayed on monitor 18. As preparation for cutting out a specimen region of interest, a cut line can be defined on monitor 18 by means of a computer mouse (not depicted) or any other cursor control device. Computer 16 is furthermore connected to laser light source 6, and delivers trigger signals to it to initiate laser pulses only when a cut is being performed.

The cut width of a laser in a specimen depends on the laser parameters, for example the laser power and the aperture of laser beam 7. This cut width is determined previously or is stored in a table in computer 16 as a function of the laser parameters. Corresponding to the presently set cut width, for the defined reference cut line a number of reference positions of the laser beam on specimen 4 is calculated, the successively arranged reference positions of laser beam 7 resulting in the desired reference cut line.

The reference positions on specimen 4 are then moved to in succession with laser scanning device 31. Each time the reference position of laser beam 7 on specimen has been prepared or set by means of laser scanning device 31, computer 16 supplies trigger signals to initiate laser pulses at laser light source 6. In this fashion, the cut line is generated in steps.

In a second method step, the webs are broken with a single laser pulse. In this embodiment, a control system, integrated into the computer, for automatic defocusing of laser 6 is provided as the means for breaking the webs. In addition, the center point of the specimen region of interest can be determined, from the preselected cut line, by a software program in computer 16. X-Y stage 2 can then be moved in such a way that the stationary, defocused laser beam 7 is directed onto this calculated center point upon breakage of the webs.

The present invention was described with reference to exemplary embodiments. It is nevertheless apparent to any person skilled in this art that changes and modifications can be made without thereby leaving the range of protection of the claims recited hereinafter.

PARTS LIST

| | |
|---|---|
| 1 | Microscope |
| 2 | Displaceable X-Y stage |
| 3 | Specimen holder |
| 4 | Specimen |
| 5 | Illumination system |
| 6 | Laser |
| 7 | Laser beam |
| 8 | Microscope stand |
| 9 | Objective |
| 10 | Optical axis |
| 11 | Condenser |
| 12 | Eyepiece |
| 13 | Optical system |
| 14 | Stop |
| 15 | Stop motor |
| 16 | Computer |
| 17 | Camera |
| 18 | Monitor |
| 19 | Collection vessel |
| 20 | Illuminating beam path |
| 21 | Imaging beam path |
| 22 | Cells |
| 23 | Specimen region of interest |
| 24 | Atypical cell structure |
| 25 | Cut line |
| 26 | Web |
| 27 | Web |
| 28 | Web |
| 31 | Laser scanning device |
| 32 | Motor for laser scanning device |
| 33 | Control unit |

What is claimed is:

1. A method for laser microdissection of specimen regions of interest of a specimen that is mounted on a specimen holder, comprising the following steps:
    a) creating a perforation with webs along a cut line, enclosing the specimen region of interest and interrupted by webs, by means of a focused laser beam, the perforation having at least two webs that interrupt the cut line and join the specimen region of interest to the surrounding specimen; and
    b) breaking the webs of the perforation with a single laser pulse of the defocused laser beam directed onto the specimen region of interest, thereby detaching the specimen region of interest from the specimen.

2. The method as defined in claim 1, wherein the diameter of the laser beam during creation of the perforation is constant.

3. The method as defined in claim 1, comprising using a laser pulse with a defocused laser beam to accomplish breakage of the webs.

4. The method as defined in claim 1, comprising defining the cut line by a user before creation of the perforation.

5. The method as defined in claim 1, comprising defining the location of the webs by a user before creation of the perforation.

6. The method as defined in claim 1, comprising defining the width of the webs is defined by a user before creation of the perforation.

7. An apparatus for laser cutting of microscopic specimens with a focused laser beam comprising:
    a) a microscope having at least one objective that defines an optical axis, for viewing of a specimen having a specimen region of interest, and having a laser that generates a laser beam and at least one optical system that couples the laser beam into the objective,
    b) a cut line control unit, associated with said microscope for generating a relative movement between said laser beam focused by the objective,
    c) perforation creating means for creating a perforated cut line around said specimen region of interest, said cut line having at least two webs that join said specimen region of interest to said surrounding specimen,
    d) means for defocusing said laser beam, and
    e) web breaking means for directing a single laser pulse of said defocused laser beam onto the specimen region of interest, thereby detaching the specimen region of interest from the specimen.

8. The apparatus as defined in claim 7, wherein the laser beam is stationary and the cut line control unit comprises a displaceable X-Y stage which moves the specimen relative to the stationary laser beam during creation of a perforation.

9. The apparatus as defined in claim 7, wherein the cut line control unit comprises a laser scanning device which moves the laser beam relative to a stationary specimen during creation of a perforation.

10. The apparatus as defined in claim 7, wherein the perforation creating means comprise a laser control unit which controls the operating parameters of the laser.

11. The apparatus as defined in claim 7, wherein the perforation creating means comprise an autofocus apparatus for the laser.

12. The apparatus as defined in claim 7, wherein the web breaking means, comprise a perforation control unit for controlling the cut line control unit and the laser control unit.

13. The apparatus as defined in claim 7, wherein the perforation control unit comprises means for defocusing the laser.

14. The apparatus as defined in claim 7, further comprising means for selection of the cut line by a user.

15. The apparatus as defined in claim 7, further comprising means for selection of the width of the webs by a user.

16. The apparatus as defined in claim 7, further comprising means for selection of the location of the webs by a user.

* * * * *